(12) United States Patent
Mendenhall (10) Patent No.: US 6,772,754 B1
(45) Date of Patent: Aug. 10, 2004

(54) BREATH ACTUATED NEBULIZER CONTROLLER APPARATUS AND METHOD

(76) Inventor: Terry Michael Mendenhall, 526 Borden Rd., San Marcos, CA (US) 92069-1868

(*) Notice: Subject to any disclaimer, the term of this patent is extended or adjusted under 35 U.S.C. 154(b) by 109 days.

(21) Appl. No.: 10/314,666

(22) Filed: Dec. 9, 2002

Related U.S. Application Data (63) Continuation-in-part of application No. 09/475,080, filed on Dec. 30, 1999, now abandoned.

(51) Int. Cl.$^7$ ............................................. A61M 11/00
(52) U.S. Cl. ........................ 128/200.14; 128/203.12; 128/205.24; 128/207.14
(58) Field of Search ................. 128/200.14–200.23, 128/200.24, 203.12, 203.15, 203.23, 204.18, 204.25, 204.23, 204.26, 205.24, 207.14–207.18; 239/569, 573; 251/12, 66, 73, 149, 213, 318, 324, 336, 337, 349, 356

(56) References Cited

U.S. PATENT DOCUMENTS

| | | | | | |
|---|---|---|---|---|---|
| 3,769,973 | A | * | 11/1973 | Esbenshade, Jr. | 128/200.14 |
| 5,570,682 | A | * | 11/1996 | Johnson | 128/200.14 |
| 5,586,551 | A | * | 12/1996 | Hilliard | 128/203.29 |
| 6,044,841 | A | * | 4/2000 | Verdun et al. | 128/200.18 |
| 6,105,929 | A | * | 8/2000 | Davenport et al. | 251/63.6 |
| 6,116,233 | A | * | 9/2000 | Denyer et al. | 128/200.18 |

* cited by examiner

Primary Examiner—Glenn K. Dawson (57) ABSTRACT

A nebulizer system includes a T-piece together with both a nebulizer and a breath-actuated controller connected to the T-piece. The nebulizer has a nebulizer inlet and the nebulizer is adapted to deliver a nebulized substance to a patient (i.e., a person) through the T-piece in response to a flow of compressed gas into the nebulizer inlet. The breath-actuated controller is adapted to be mounted on the distal end portion of the T-piece and to interrupt the flow of compressed gas into the nebulizer inlet while the patient is not inhaling through the T-piece.

2 Claims, 6 Drawing Sheets

BREATH ACTUATED NEBULIZER CONTROLLER APPARATUS AND METHOD

CROSS REFERENCE TO RELATED APPLICATION

This application is a continuation in part of U.S. patent application Ser. No. 09/475,080 filed Dec. 30, 1999 now abandoned.

BACKGROUND OF THE INVENTION

1. Technical Field

This invention relates generally to medical apparatuses, and more particularly to a medical apparatus and method for delivering inhaled liquid medication through a nebulizer with controlled efficiency achieved through breath actuation of a continuous flow nebulizer.

2. Description of Related Art

Medical nebulizers deliver an aerosol form of liquid medication that can be inhaled by a patient (i.e., a person) for various pulmonary problems. They are increasingly becoming applicable to non-pulmonary patients using the respiratory mucosa as a means for systemic delivery of medications. For additional related background information, refer to U.S. Pat. Nos. 1,109,318; 2,432,946; 3,769,973; 4,174,712; 4,259,951; 4,823,784; 5,020,530; 5,062,419; 5,165,392; 5,396,883; 5,398,673; 5,427,089; 5,813,401; 5,823,179; and 5,865,171.

In most nebulizers, liquid medication is aerosolized by using a compressed gas source of air, oxygen, or a mixture of several gases to generate a flow of medication continuously. The patient inhales and exhales through a mouthpiece attached to a nebulizer with an open or valved circuit. One problem with these methods of continuous nebulization, is wasted medication during a patient's exhalation, or pausing to cough, talk, rest, and so forth.

Also, the wasted medication is vented to the surrounding environment which can expose other people nearby, including medical personnel, visitors, family members, and patients. Another possible problem may be contamination of the nebulizer and circuit caused by the patient exhaling back through the nebulizer circuit. The continuous flow of medication either in an open or closed circuit complicates the ability to accurately regulate dosages because of waste or excessive condensation. Finally, it has been suggested that some present and future medication's integrity may be compromised by excessive continuous nebulizing action.

Accordingly, with these considerations taken into account, there is a need for intermittent nebulization with minimal efforts provided by a patient's breathing cycle.

The present invention solves the problem of nebulizers which deliver medication and nebulize continuously, and it decreases contamination, by using the patient's breathing cycle to automatically control the delivery of medication to the patient. The invention is an uncomplicated key-valve control attached to a nebulizer for medication delivery to the lungs. This key-valve control attaches distally to a typical nebulizer using a typical T-piece tubing fitted on the outlet of a nebulizer, and utilizing a typical one-way valve attached proximally between the mouthpiece and T-piece tube. The key-valve control allows the compressed gas source to be diverted to a nebuilizer only during the patient's inhalation phase with minimal breathing efforts. This invention also allows exhalation through any simple one-way valve at the mouthpiece, and not through the nebulizer, thereby decreasing possible contamination of the nebulizer.

The structure of the preferred embodiment includes two tubes combined as one unit, one outer tube with an inner ring and one smaller inner tube with an inlet hole. The inlet hole is connected to a compressed gas source utilizing a small tubing with a Y-connector at its distal end. One end of the Y-connector attaches to the nebulizer gas inlet, and the other end to the compressed gas source using a typical oxygen tubing.

A solid internal valve-key cylinder with ribbed ends spaced on the distal portion, and a valve at the other end, slides axially within the inner tubing. By this piston action, the space between the ribs of the valve-key align with the inlet hole during inhalation in order to thereby direct the compressed source flow to the nebulizer during inhalation. Also, the ribbed space moves distally during exhalation in order to thereby allow the compressed gas source to escape through the outer tubing through vents at the proximal end of the inner tubing chamber. The valve-key is held in place by a post inserted through the outer tubing at a proper distance to allow correct movement. A spring mechanism on the post pushes the valve-key back to its exhaled resting position. This internal valve-key should be fitted within the inner tubing as tightly to the least amount of tolerance for the patient to easily initiate the required piston action of the invention. This can be accomplished using current medically approved plastic polymers.

This invention thereby allows nebulization by a currently used nebulizers only when the patient is inhaling the aerosolized medication, and it prevents exhalation back through the nebulizer. This, therefore, prevents waste, reduces contamination of the nebulizer, minimizes medication exposure to others, and allows more accurate dosing of medication.

DESCRIPTION OF THE PREFERRED EMBODIMENTS

The following description is provided to enable any person of ordinary skill in the art to construct and use the invention, and it sets forth the best embodiments contemplated by the inventor of carrying out the invention. Various modifications, however, will remain readily apparent to those of ordinary skill in the art, since the generic principles of the present invention have been defined herein specifically to provide for an improved means to nebulize medications using current prior art as show in FIG. 1, such as a continuous flow aerosol nebulizer 14 having a nebulizer inlet 14A for receiving a flow of compress gas from a source 10 of compressed gas and a nebulizer outlet 14B for delivering a nebulized substance to a T-piece 16. The T-piece 16 has a one-way valve 8, a mouthpiece 18, a T-piece inlet 16A, and a T-piece distal end portion 16B, all as is commonly utilized in the respiratory medical field.

Figure 2:
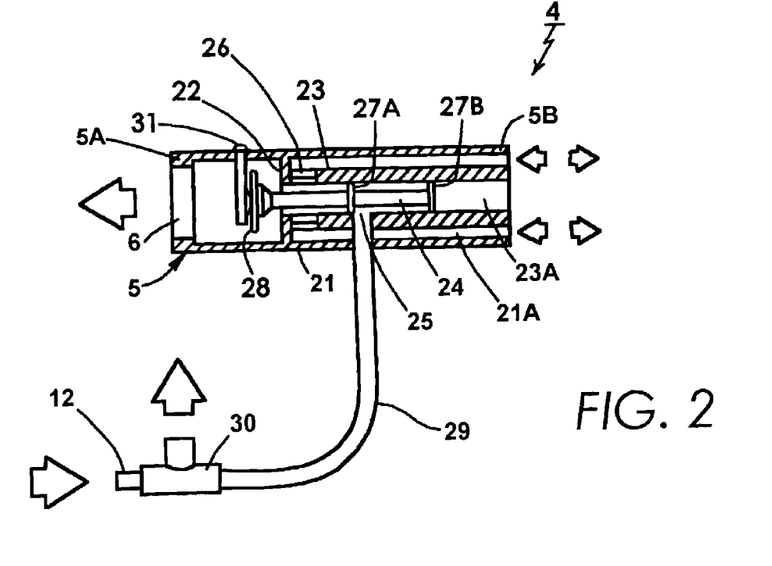
FIG. 2 is a cross section side view of the preferred embodiment of the invention along the axis of the distal end of the T-piece shown in the condition when the patient inhales.
Figure 3:
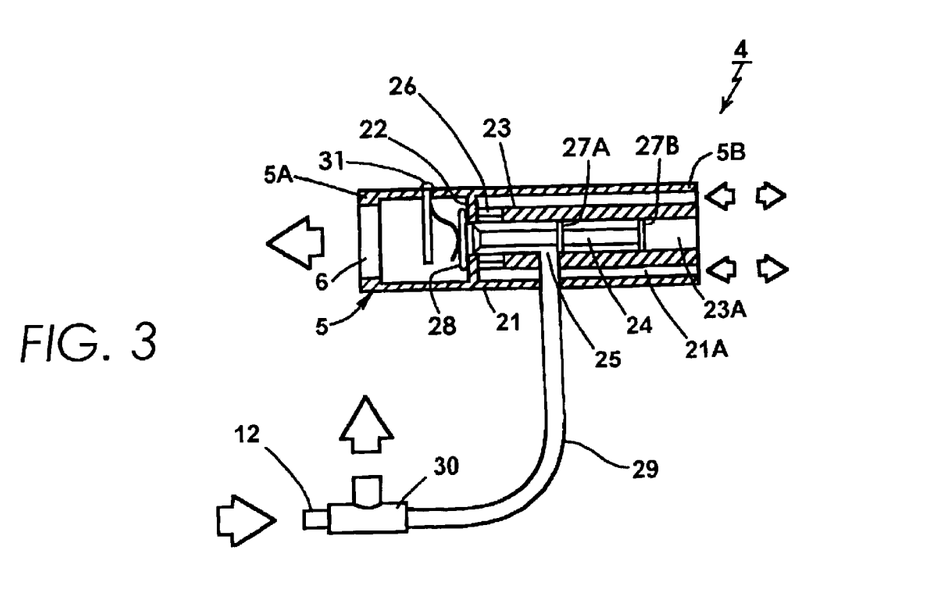
FIG. 3 is a cross section side view of the preferred embodiment of the invention along the axis of the distal end of the T-piece shown in the condition when the patient exhales.

This invention of a breath actuated nebulizer controller valve 4 shown in FIG. 2 and FIG. 3 operates to activate and inactivate nebulization using minimal patient respiratory efforts. FIG. 2 and FIG. 3 depict the same structure of the preferred embodiment of a control valve 4 in a side view in its two phases of operation. FIG. 2 shows a side view of the invention in its inhalation phase and FIG. 3 shows a side view in its exhalation phase. The control valve 4 can be typically formed from medically approved plastic polymers.

Figure 1:
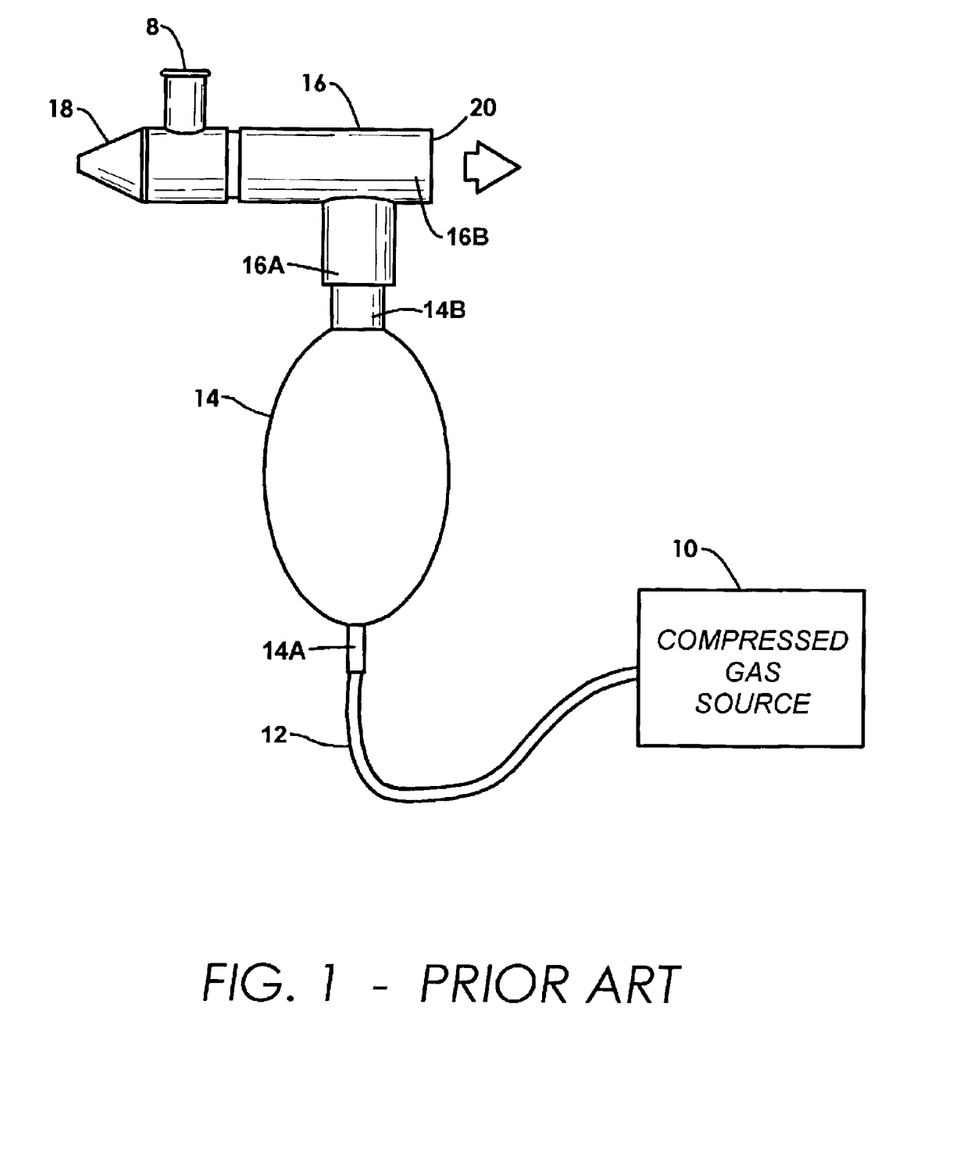
FIG. 1 is a diagram of a typical prior art apparatus to which the invention is attached.
Figure 4:
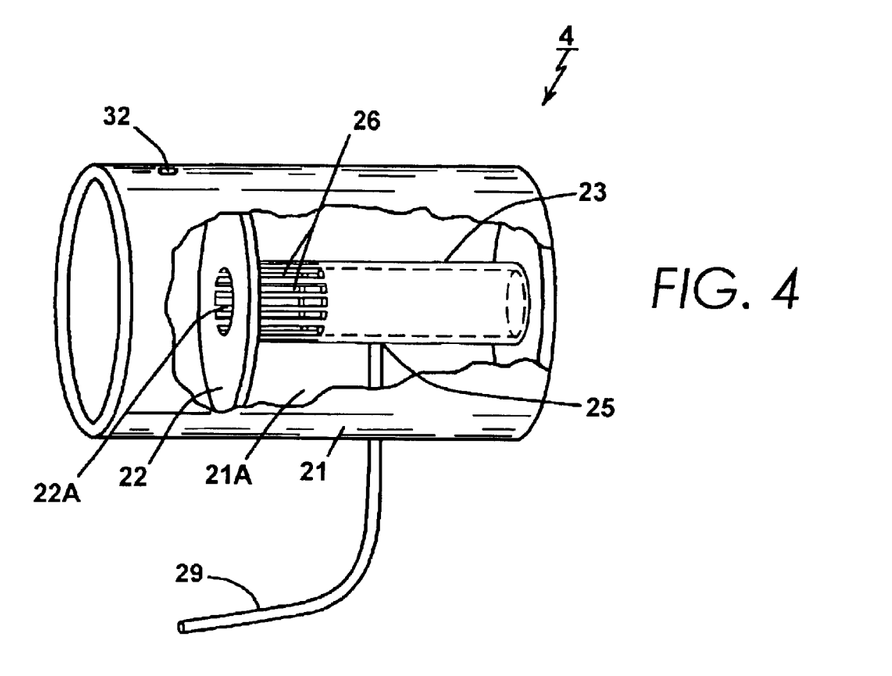
FIG. 4 is an enlarged side view cut away drawing of the preferred embodiment of the main cylindrical body of the invention.

The molded housing 5 has a proximal end portion 5A that fits on the distal end portion 16B of the T-piece 16 in FIG. 1 and a distal end portion 5B that provides a vent to the atmosphere. The proximal end portion 5A is adapted to be mounted (removably) on the T-piece distal end portion 16B as an extension of the T-piece distal end portion 16B. The proximal end portion 5A is cylindrically shaped and it slides coaxially onto the T-piece distal end portion 16B with a tight fit, thereby maintaining the proximal end portion 5A of the housing 5 in fluid communication with the T-piece distal end portion 16B. The proximal end portion 5A defines a first port 6 (FIGS. 2, and 3) that is in fluid communication with the T-piece 16 and a second port or hole 25. The housing 5 is essentially two cylindrical tubes, an outer tube 21 and an inner tube 23 that are connected together as one piece by a flat inner wall 22, with an opening 22A (FIG. 4) the same size as the cylindrical shaped inner tube chamber 23A (FIGS. 2 and 3) of the inner tube 23. Also part of this molded plastic design is the hole 25. A feeding tube 29 functions as means for coupling the second port of the housing 5 (i.e., the hole 25) to the nebulizer inlet 14A for purposes of diverting a flow of compressed gas from the source 10. FIG. 4 is an enlarged side view of the molded plastic design of the control valve 4. There are vents 26 in the portion of the inner tube 23 that extend from the wall 22 to where the first rib seal 27A would not reach during inhalation as described in FIG. 2. Finally, as part of this molding, a hole 32 (FIG. 4) placed and sized properly to allow a blocking post and spring 31 (FIGS. 2, 3, and 6) to be inserted into the outer tubing chamber 21A (FIGS. 2 and 3).

Figure 5:
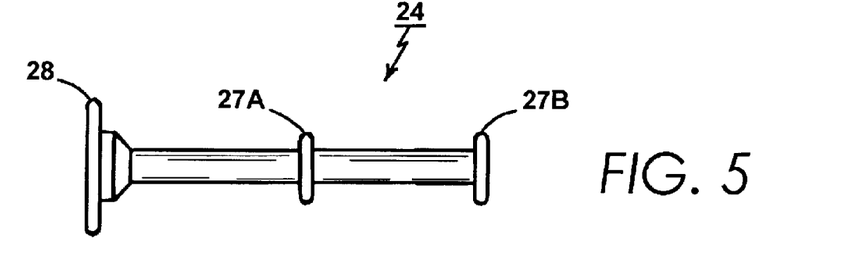
FIG. 5 is an enlarged side view of the preferred embodiment of the valve-key part that slides axially fitted within the inner portion of the small inside tube.
Figure 7:
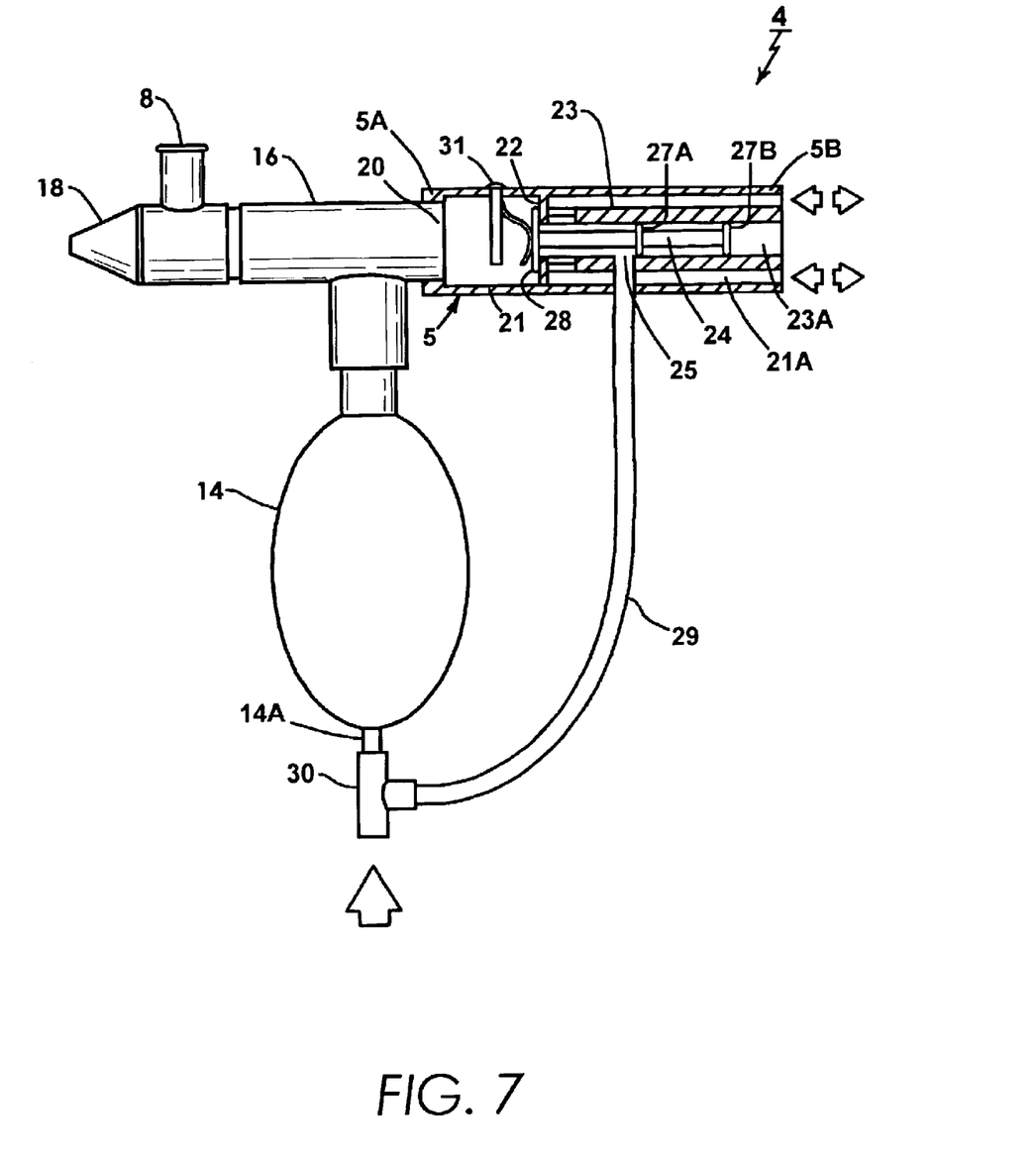
FIG. 7 is a side view drawing showing the preferred way a prior art nebulizer and the invention can be attached together.

Inserted into the inner tube chamber 23A axially through the flat inner wall 22, is a valve-key 24 that includes a breath-actuated actuator element referred to herein as a wafer valve 28 (FIGS. 2 and 3). When the patient inhales, the wafer valve 28 opens to the open position shown in FIG. 2 to allow entrained air as needed by the patient. As the wafer valve 28 opens, the valve-key 24 moves to the position shown in FIG. 2 so that the inner tube chamber 23A is occluded by the ribs of the valve-key 24. That stops the gas flow through the inlet hole 25, and that initiates nebulization during inhalation, as shown in FIG. 2. The wafer valve 28 alternately closes to the position shown in FIG. 3 to allow no exhaled air out, except through the one-way exhalation valve 8 that is attached between the mouthpiece 18 and the T-piece 16 (FIG. 7). At least two ribbed seals 27A and 27B on the valve-key 24 are properly aligned and sized to allow diverting the compressed gas source out through the vents 26 (FIGS. 2, 3, and 4) into the outer tube chamber 21A of the outer tube 21, and from there to the environment during exhalation as shown in FIG. 3. The valve-key 24 is shown enlarged in FIG. 5. The shape of the valve-key 24 from the wafer valve 28 is as large as the inside diameter of the inner tube 23 (i.e., the diameter of the inner tube chamber 23A) for a distance equal to the distance needed for the first rib 27A to cross completely over the diameter of the inlet hole 25 to the position shown in FIG. 3. Then, the shape is at least half in size until the first rib seal 27A. At that point, the outside diameter of the valve-key 24 is preferably one-half the inside diameter of the inner tube 23 until the end of the second rib seal 27B.

Figure 6:
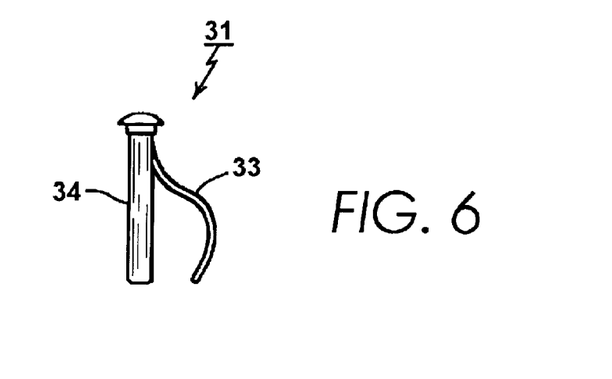
FIG. 6 is an enlarged side view of the preferred embodiment of the blocking post and spring that is inserted into the main cylindrical body of the invention.

FIG. 6 shows an enlarged drawing of the preferred design of the blocking post and spring 31. It is one part and it can be made of a plastic polymer to include a split and properly tensioned spring 33 to assist in returning the valve-key 24 to its resting exhalation state shown in FIG. 3, and a post 34 to block the valve-key 24 at a proper distance as shown in FIG. 2 for correct function. The post 34 can be inserted into the outer tube 21 to be able to come in contact with the valve-key 24 at the wafer valve 28.

It can be appreciated that the position and type of the blocking post and spring 31 could be designed in many ways and that this is just one preferred design to show function. Stated another way, the components within the housing 5 are a valve assembly that is adapted to function as means responsive to the patient not inhaling through the T-piece for coupling the second port (hole 25) in fluid communication with the environment while the patient is not inhaling through the T-piece in order to thereby interrupt the flow of compressed gas into the nebulizer and the delivery of the nebulized substance to the T-piece inlet while the patient is not inhaling through the T-piece.

FIG. 7 is the prior art nebulizer system shown in FIG. 1 combined with the control valve 4. The prior art nebulizer system and the control valve 4 are connected to each other via the T-piece tube 16 and a Y-connector 30 to achieve controller function. Again, it is appreciated and apparent that for one of ordinary skill in the art, other means of connection are possible.

Figure 8:
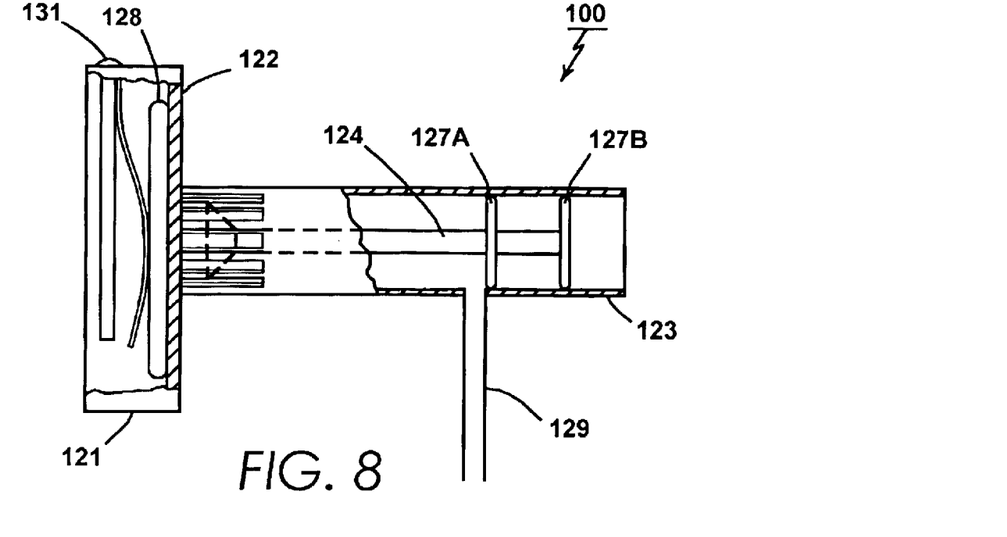
FIG. 8 is an enlarged side view cut away drawing of an alternative embodiment using only the cylindrical inner chamber of the invention.

FIG. 8 is a side view of an alternative embodiment 100 using only one tube 123 designed to be similar to the inner tube 23 of the control valve 4, without the outer tube 121 extending over the inner tube 123 from the wall 122. Also, the size and shapes of these embodiments can be any of many desired by a manufacturer of this breath-actuated nebulizer controller invention. Reference numerals designating parts of the alternative embodiment 100 are increased by one hundred over those designating related parts of the control valve 4, including a valve-key 124 that includes a wafer valve 128 and ribs 127A and 127B controlling the flow through tubing 129.

Figure 9:
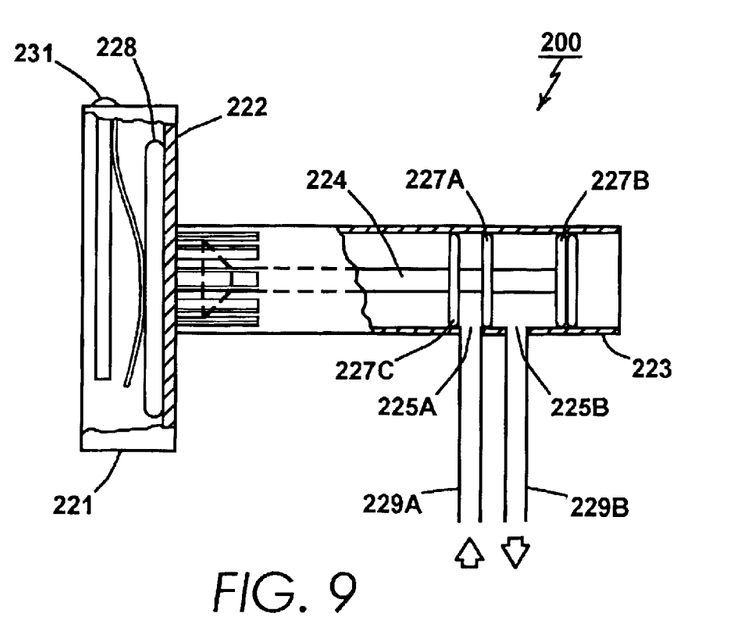
FIG. 9 is an enlarged side view cut away drawing of a second preferred embodiment of the cylindrical inner chamber and valve-key of the invention to stop compressed gas, instead of diverting the flow, by using two rib sealed chambers, an inlet hole with tubing attached to a compressed gas source, and an outlet hole with tubing connected to the nebulizer inlet.

Finally, a control valve 200 constructed according to the invention may include properly spaced ribs 227A, 227B, and 227C on the valve-key 224 to create two separate chambers. Properly spaced outlet holes 225A and 225B are provided in the inner tube 223 as second and third ports, one (the second port) for tubing 229A attached to the compressed gas source, which tubing 229A functions as means for coupling the second port of the housing in fluid communication with the source of compressed gas and the other (the third port) for tubing 229B attached to the nebulizer inlet, which tubing 229B functions as means for coupling the third port of the housing in fluid communication with the nebulizer inlet (as illustrated in the side view in FIG. 9). This is a variation of the invention that allows occlusion of the compressed gas source instead of diverting the flow as done by the control valve 4. The control valve 200 is similar in concept to that of the control valve 4, except in reducing the waste of compressed gas source. This alternative embodiment would be useful when there is a limited supply of a compressed gas source, for example. Reference numerals designating parts of the control valve 200 are increased by two hundred over those designating related parts of the control valve 4, including an outer tube 221, an inner tube 223, a wafer valve 228, and wall 222, and a blocking post and spring 231. Stated another way, the valve assembly within the housing is adapted to function as means responsive to the patient breath through the T-piece for (i) coupling the second port of the housing in fluid communication with the third port of the housing while the patient is inhaling through the T-piece in order to thereby enable the delivery of the nebulized substance from the nebulizer outlet to the T-piece inlet when the patient inhales through the T-piece, and (ii) for de-coupling the second port of the housing from the third port of the housing while the patient is not inhaling through the T-piece in order to thereby interrupt the delivery of the nebulized substance to the T-piece inlet while the patient is not inhaling through the T-piece.

Figure 10:
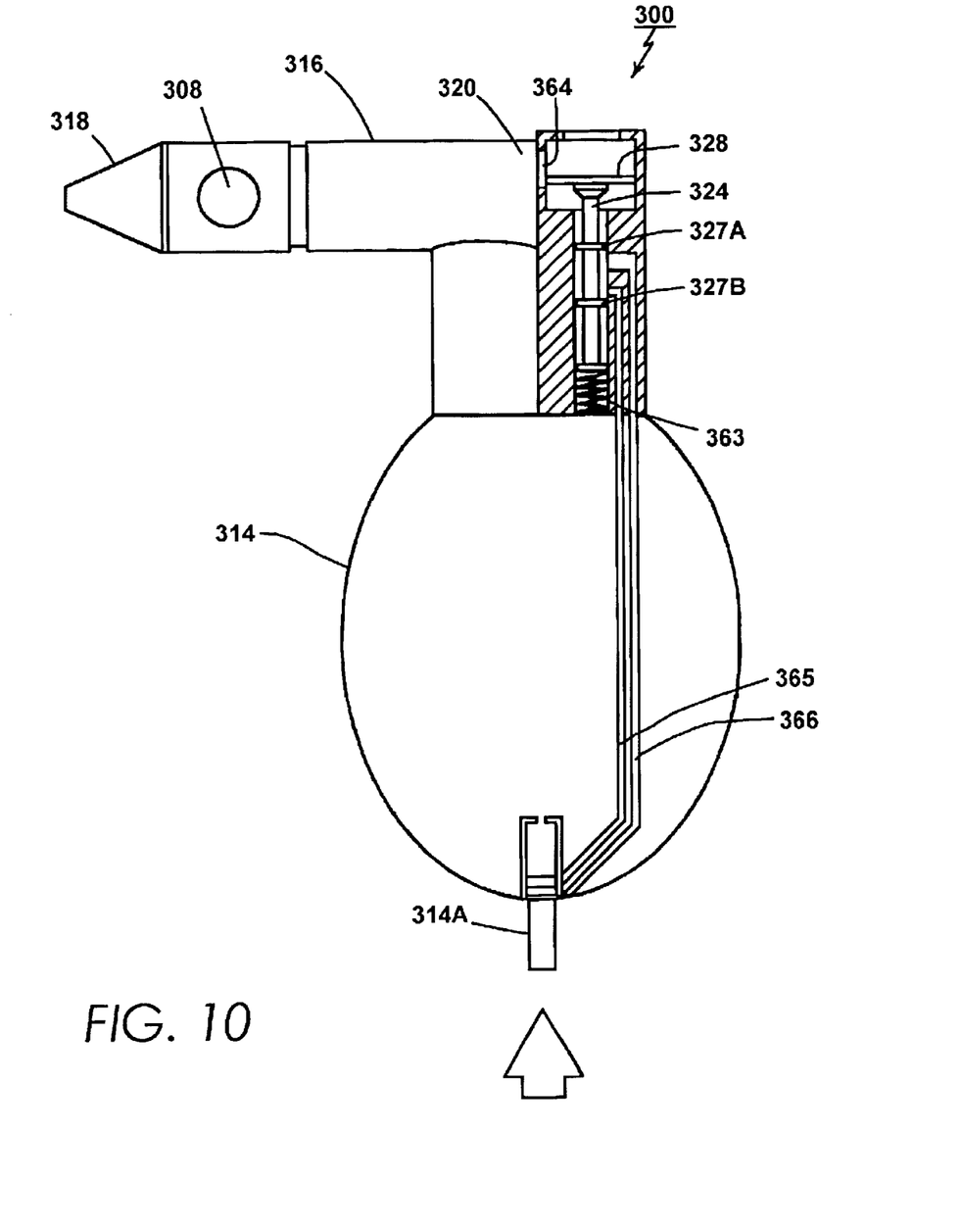
FIG. 10 is a side view of another alternative embodiment that is miniaturized in order to fit within a nebulizer as part of the nebulizer.

Also, as shown in the enlarged side view in FIG. 10, this invention can be adapted to function within and as part of a prior art nebulizer 314 that is similar to the prior art nebulizer shown in FIG. 1. That is accomplished by miniaturizing the components to fit vertically within a nebulizer chamber of the prior art nebulizer 314, and by reversing the wafer 328 and valve-key 324 piston action as shown in FIG. 10. The valve-key 324 is shown activated during the inhalation phase with outside vented air entertainment and block, and a push spring system using the same concept and design means of the preferred embodiment in FIGS. 2–7 and the alternative embodiment in FIG. 9. Also shown as prior art are a mouthpiece 318 and a one-way valve 308 for exhalation that needs to be attached to the nebulizer 314 for proper patient usage. Reference numerals designating parts of the combined nebulizer and control valve 300 are increased by three hundred over those designating related parts of the nebulizer 14 and control valve 4, including a nebulizer compressed gas inlet 314A, a T-piece 316 with a distal end 320, a valve-key 324 with a wafer valve 328, ribs 327A and 327B, a spring 363, and a fluid-communicating port 364.

Thus, the first embodiment of the invention is a nebulizer system having a control valve 4 activated by pressure changes in a patient's breathing cycle for intermittent nebulization of medication. The control valve is attached to a typical nebulizer T-piece tube 16 having a mouthpiece 18 and a one-way valve 8 for exhalation. It is also attached to a Y-connector 30 (FIG. 7) that communicates gas through the tubing 12 (FIG. 1) from the compressed gas source 10 to a gas inlet 14A of the nebulizer (FIG. 7). The control valve 4 includes two straight hollow tubes 21 and 23, one within the other, that are attached by an inner ring around one-half inch inside the outer tube 21, at the front end of the inner tube toward the end that attaches to the T-piece tube 16. The tubing 29 communicates gas from the Y-connector 30 to the inner tube 23. The valve-key 24 moves in a piston action to cause ribs 27A and 27B to occlude the inlet hole 25 during inhalation and alternately to close the valve-key 24 to its diverted exhalation or resting position (non-nebulizing phase) during exhalation or non-use where it diverts the pressurized gas flow to the environment. In other words, the control valve 4 is adapted to function as means responsive to a patient breathing through the T-piece 16 for interrupting the flow of compressed gas into the nebulizer inlet 14A while the patient is not inhaling through the T-piece 16 (i.e., exhaling or non-use) and for not interrupting the flow of compressed gas into the nebulizer inlet 14A while the patient is inhaling through the T-piece 16.

Stated another way, the invention is an apparatus and method for controlling a nebulizer used in respiratory therapy that switches compressed gas to the nebulizer only during inhalation efforts of the patient receiving nebulized medication. The preferred structure of the controller (i.e., the control valve 4) attaches to the distal end 20 of the T-piece tube 16 mounted atop the nebulizer 14, with the one-way exhalation valve 8 and the mouthpiece 18 attached to the patient'send of the T-piece. The tubing 29 is attached by the Y-connector 30 to the nebulizer's gas source inlet 14A (FIG. 7) and the compressed gas tubing 12 (FIG. 1). The controller includes a valve-key 24 that moves within a cylinder (i.e., the interior of the inner tube 23) in a piston action to direct the compressed gas source 10. The valve-key structure of a post with the ribs 27A and 27B form a movable chamber that slides across the compressed gas inlet hole 25 to occlude during inhalation efforts of the patient and thereby initiate nebulization. When the valve-key returns to its resting state, it opens the inlet hole 25 to thereby allow compressed gas flow to be diverted away from the nebulizer, and to allow the patient to exhale out through the one-way exhalation valve 8. According to another aspect, the controller can be structured to divert flow to the nebulizer and occlude flow by using one or two rib-sealed chambers that slide across inlet and outlet holes 225A and 225B as depicted in FIG. 9. The inlet hole 225A is connected to the compressed gas source 10 and the outlet hole 225B is connected to the nebulizer inlet initiating nebulization when the chamber is common to both the inlet hole 225A and the outlet hole 225B, thereby completing a circuit only during inhalation. This second method can be miniaturized to fit within and be a part of the nebulizer 314 as depicted in FIG. 10.

What is claimed is:

1. An apparatus for controlling a nebulizer that is adapted to deliver a nebulized substance to a patient through a T-piece in response to a flow of compress gas into the nebulizer from a source of compressed gas, said nebulizer having a nebulizer inlet for receiving the flow of compress gas and a nebulizer outlet for delivering the nebulized substance to the T-piece, and said T-piece having a T-piece inlet coupled to the nebulizer outlet and a T-piece distal end portion for venting gas exhaled by the patient, the apparatus comprising:

a housing having first and second ports, which housing is adapted to be mounted on the T-piece distal end portion as an extension of the T-piece distal end portion, with the first port of the housing in fluid communication with the T-piece distal end portion;

means for coupling the second port of the housing in fluid communication with the nebulizer inlet; and a valve assembly within the housing that is adapted to function as means responsive to the patient not inhaling through the T-piece for coupling the second port in fluid communication with the environment while the patient is not inhaling through the T-piece in order to thereby interrupt the flow of compressed gas into the nebulizer inlet and the delivery of the nebulized substance to the T-piece inlet while the patient is not inhaling through the T-piece.

2. An apparatus for controlling a nebulizer that is adapted to deliver a nebulized substance to a patient through a T-piece in response to a flow of compress gas into the nebulizer from a source of compressed gas, said nebulizer having a nebulizer inlet for receiving the flow of compress gas and a nebulizer outlet for delivering the nebulized substance to the T-piece, and said T-piece having a T-piece inlet coupled to the nebulizer outlet and a T-piece distal end portion for venting gas exhaled by the patient, the apparatus comprising:

a housing having first, second, and third ports, which housing is adapted to be mounted on the T-piece distal end portion as an extension of the T-piece distal end portion, with the first port of the housing in fluid communication with the T-piece distal end portion;

means for coupling the second port of the housing in fluid communication with the source of compressed gas;

means for coupling the third port of the housing in fluid communication with the nebulizer inlet; and a valve assembly within the housing that is adapted to function as means responsive to the patient breath through the T-piece for (i) coupling the second port of the housing in fluid communication with the third port of the housing while the patient is inhaling through the T-piece in order to thereby enable the delivery of the nebulized substance from the nebulizer outlet to the T-piece inlet when the patient inhales through the T-piece, and (ii) for de-coupling the second port of the housing from the third port of the housing while the patient is not inhaling through the T-piece in order to thereby interrupt the delivery of the nebulized substance to the T-piece inlet while the patient is not inhaling through the T-piece.

* * * * *